United States Patent [19]

Pasternak et al.

[11] Patent Number: 5,326,440
[45] Date of Patent: Jul. 5, 1994

[54] PHOTOOXIDATION OF HYDROCARBONS

[75] Inventors: Mordechai Pasternak, Spring Valley; Abraham Morduchowitz, Monsey, both of N.Y.

[73] Assignee: Texaco Inc., White Plains, N.Y.

[21] Appl. No.: 990,493

[22] Filed: Dec. 14, 1992

[51] Int. Cl.$^5$ .......................... C07C 3/00; C07C 7/00
[52] U.S. Cl. ........................ 204/157.15; 210/748; 204/157.65; 204/157.9
[58] Field of Search ............... 210/748; 204/157.65, 204/157.9, 157.15, 157.3

[56] References Cited

U.S. PATENT DOCUMENTS

| | | | |
|---|---|---|---|
| 3,099,613 | 7/1963 | Bartok et al. | 204/157.9 |
| 4,045,316 | 8/1977 | Legan | 204/157.3 |
| 4,152,230 | 5/1979 | Edwards et al. | 204/157.87 |
| 4,383,904 | 5/1983 | Shepherd | 204/157.69 |
| 4,571,290 | 2/1986 | Ward et al. | 204/157.69 |

OTHER PUBLICATIONS

CA98 (22): 185157w "Photooxidation of diphenylmethane and 1,2,3,4 tetrahydronapthalene as a liquid film on water."

Primary Examiner—John Niebling
Assistant Examiner—C. Delacroix-Muirheid
Attorney, Agent, or Firm—George J. Darsa

[57] ABSTRACT

Photooxidation of cyclohexene or tetralin is effected preferably in the presence of a photosensitizer such as an aliphatic ketone by light of wave length of about 2000 Å–7000 Å to form hydroperoxide, alcohol, and ketone products in good photoconversion yield and selectivity.

12 Claims, No Drawings

PHOTOOXIDATION OF HYDROCARBONS

FIELD OF THE INVENTION

This invention relates to the oxidation of hydrocarbons. More particularly it relates to the photooxidation of compounds typified by tetralin or cyclohexene.

BACKGROUND OF THE INVENTION

As is well known to those skilled in the art, various hydrocarbons have been oxidized to produce desired products. Illustrative of disclosures setting forth such reactions are the following:

(i) German Patent DE 3,229,001 to Union Carbide as assignee of R. Wilson discloses oxidation of tetralin in the presence of a carboxyl-containing ion exchanger which preferably has been modified with Cr ions and an amine such as 5-ethyl-2-methyl pyridine.

(ii) USSR SN 924,032 to Terpugova et al (as reported at Chem. Abstr. 97: 182,013 q) discloses oxidation of tetralin to prepare alpha-tetralone at 60° C.-120° C. in the presence of polydehydrobutoxychrysoidine.

(iii) USSR 825,480 to Borisenkova et al (as reported at Chem. Abstr 95:115,134 a) discloses oxidation of tetralin at 80° C.-150° C. with an oxygen-containing gas in the presence of Co or Fe phthalocyanine.

(iv) Japan Kokai 78 18,553 to Imamura et al (as reported at Chem. Abstr. 88:169,830 y) discloses oxidation of tetralin at 30° C.-120° C. with oxygen in various liquids in the presence of Co carboxylate or nitrate.

(v) Japan Kokai 76 48643 to Kudo et al (as reported at Chem. Abstr. 85:62,856 x) discloses oxidation of tetralin in the presence of catalyst comprising Cr salts of $C_5$–$C_{25}$ organic acid plus aliphatic amines or quinolines.

(vi) Japan Kokai 75 58044 to Kudo et al (as reported at Chem Abstr 85: 114,075 x) discloses oxidation of tetralin in the presence of Cr oxide and lutidine.

Other references related to photooxidation may include:

(vii) K. Gollnick *Photooxidation and its Application in Industry* La Chimica E L' Industria, V 64, N.3, Mar. 20, 1982 and references cited therein.

(viii) M. Pasternak and A. Morduchowitz *Photochemical Oxidation and Dimerization of Alkylbenzenes* Tet. Let. Vol 24, 4275 (1983) and references cited therein.

Continuing attempts are being made to provide a process for oxidation of compounds such as tetralin and cyclohexene in order to permit attainment of desired products under more favorable controlled conditions.

It is an object of this invention to provide a novel process for oxidizing compounds such as tetralin and cyclohexene. Other objects will be apparent to those skilled in the art.

STATEMENT OF THE INVENTION

In accordance with certain of its aspects, this invention is directed to a method which comprises maintaining in liquid phase a charge liquid containing

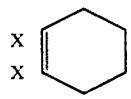

wherein X is hydrogen or together both X's form a 1,3-butadiene chain cyclized to form a benzene ring;

contacting said charge liquid with oxygen during a photooxidation reaction at photooxidation conditions;

irradiating said charge liquid with light of wave length of 2000 Å–7000 Å during a photooxidation reaction at photooxidation conditions thereby forming reaction medium containing oxidized charge liquid; and recovering said reaction medium containing oxidized charge liquid.

DESCRIPTION OF THE INVENTION

The charge compositions which may be employed in practice of the process of this invention may include those of the formula

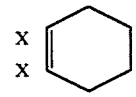 (I)

wherein X is hydrogen or together both X's form a 1,3-butadiene chain cyclized to form a benzene ring.

It will be apparent to those skilled in the art that when X is hydrogen, the charge composition may be cyclohexene (I). When together both X's form a 1,3-butadiene chain cyclized to form a benzene ring, the charge composition may be tetralin (II):

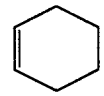

(I)

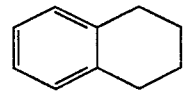

(II)

Although it may be possible to carry out the process of this invention by dissolving the charge composition in inert diluent-solvent, typified by hydrocarbons such as toluene, xylene, etc. or ethers typified by tetrahydrofuran, dibutyl ether, etc., it is preferred to carry out the process without solvent i.e. neat.

Reaction is carried out in liquid phase typically at 0° C.–150° C., preferably at 20° C.–80° C., most preferably at ambient room temperature of about 25° C. and pressure of 0–200 psig, preferably 0–50 psig, most preferably at atmospheric pressure.

It is a feature of this invention that the photooxidation may be carried out by contacting the charge liquid with oxidizing agent during a photooxidation reaction. The oxidizing agent may be preferably a source of oxygen—typically air, oxygen-enriched air, or most preferably substantially pure oxygen.

Photooxidation is typically carried out in the presence of light. It has been observed that high energy radiation (i.e. that of wave length below about 2000 Å) possesses sufficient energy to accomplish the desired transformation—but unfortunately it is so energetic that it decomposes many of the components of the reaction mixture. Although it may also be possible to utilize radiation containing wave lengths above about 7000 Å, it is observed that the energy is so low that the yield is undesirably low even after a long period of time.

Accordingly it is found desirable to carry out the reaction using radiation falling in the region of about 2000 Å–7000 Å. Preferably the wave length is above 2800 Å (in the near ultraviolet spectrum) and more preferably 2800 Å–3000 Å.

Control of the Conversion and Selectivity in practice may commonly be effected by employing a mercury vapor light (which yields a spectrum of light of 2200 Å–5800 Å) which is mounted with various absorption sleeves which cut out light below designated wave lengths. No particular advantage is attained by the presence of radiation above about 5800 Å but no special effort need be expended to remove radiation in this range.

Absorption and elimination of light falling below the desired wave length (i.e. above the desired energy level) may typically be effected by using the following absorption sleeves on the light from the mercury vapor lamp:

TABLE

A. A sleeve of pyrex glass which absorbs radiation below about 2800 Å.
B. A sleeve of uranium salt glass which absorbs radiation below about 3300 Å.
C. A sleeve of soda-lime glass which absorbs radiation below about 4000 Å.
D. A sleeve of quartz glass which absorbs radiation below about 2100 Å.

It should be noted that sunlight (3000 Å–14000 Å) may be employed—but since only 5% of the emission spectrum is below 4000 Å, an undesirably low yield is attained in reasonable time.

Oxidation is typically carried out over 12–48 hours, preferably 24–36 hours, say 24 hours. During this reaction period, oxygen-containing gas, preferably oxygen, is bubbled through the agitated reaction medium.

Photooxidation occurs to convert the charge composition to desired products. Typically the Conversion (defined as the w % of charge converted to products) is 4–20 w %, say about 13 w % after about 24 hours of irradiation with 450 watts medium pressure mercury vapor lamp—10 cm from the charge.

During reaction, the charge hydrocarbon is photo oxidized to hydroperoxide, alcohol, and ketone.

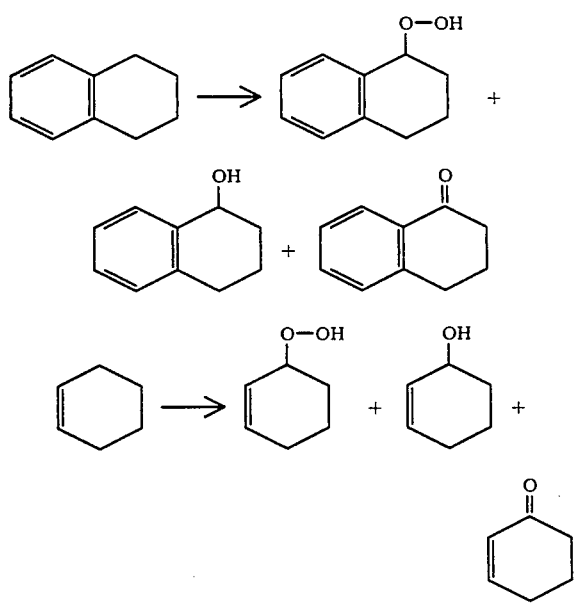

In the case of tetralin charge, the Conversion may be 4–15 w %, say 12.9 w %. Selectivity may be 18–65 w %, say 22.3 w % to alpha-tetralol, 16–50 w %, say 18.4 w % to alpha tetralone, 12–70 w %, say 18.4 w % to alpha-tetralone hydroperoxide.

In the case of cyclohexene charge, the Conversion may be 4–25 w %, say 19.9 w %. Selectivity may be 0–50 w %, say 10.7 w % to 2-cyclohexene-1-ol, 10–100 w %, say 50 w % to 2-cyclohexen-hydroperoxide, and 0–60 w %, say 24.1% to 2-cyclohexene-1-one.

The Selectivity to various reaction products may be modified by carrying out the photooxidation at different wave lengths. In the case of tetralin for example, use of radiation of wave length at the lower end of the useful spectrum (e.g. down to 2800 Å) will permit recovery of alcohol, and ketones in amount greater than that attained at say 3300 Å. Conversely if the hydroperoxide is desired (at the expense of the alcohol product) operation above 3300 Å is preferred to operation as low as 2800 Å. When RuCl$_2$ is present (see infra) at wave lengths above about 4000 Å only alcohol and ketone (with little or no hydroperoxide) are formed although at low photoconversion yield.

In the case of cyclohexene, increased production of ketone product is generally attained at a wave length of 2800 Å–3300 Å.

It is a feature of the process of this invention that it is preferably carried out in the presence of a photoinitiator/sensitizer which aids in transfer of energy to the charge composition. A photosensitizer may also serve as photoinitiator and abstracts hydrogen to form reactive sites. A preferred class of sensitizers/photoinitiators is that containing ketone functionality including aliphatic ketones such as acetone, 2-butanone (i.e. methyl ethyl ketone), etc. Aromatic ketones may be employed typified by benzophenone or xanthone. Ketones containing both aromatic and aliphatic moieties (such as acetophenone) may be employed. Quinones such as anthraquinone, or azo compounds (such as azobisiso butyronitrile) or polycyclic hydrocarbons (such as anthracene) may also be employed as photosensitizers. Dyes (such as methylene blue) may also be photosensitizers when the irradiation is carried out in the visible range above 4000 Å.

Photoinitiators/sensitizers may also be compounds of metals of Group VIII (those designated Groups 8, 9, and 10 in the New Notation) including Iron Fe, Cobalt Co, Nickel Ni, Ruthenium Ru, Rhodium Rh, Palladium Pd, Osmium Os, Iridium Ir, and Platinum Pt. Preferred of this group is ruthenium, preferably RuCl$_2$ as its dipyridyl complex. Other specific compounds which may be employed may include:

TABLE

FeCl$_2$
Co(NO$_3$)$_2$
Ni(NO$_3$)$_2$
PdCl$_2$

When photoinitiator/sensitizers are employed, they may be present in amount of 1–10 parts, say 5 parts per 100 parts of charge composition.

Use of photoinitiator/sensitizer is desirable in that it increases photoconversion yield and converts the hydroperoxide in the product mix to the more desirable alcohols and ketones.

It is observed that different photoinitiator/sensitizers permit attainment of different photoconversion yield and product ratios. For example, highest conversion may be attained using 2-butanone, benzophenone, or acetophenone. Xanthone produces low photo yields; but it is very efficient in converting the hydroperoxides to alcohols and ketones. (Control experiments indicate that these reactions do not proceed at room temperature in the absence of light).

Practice of the process of this invention will be apparent to those skilled in the art from the following specific examples wherein all parts are parts by weight unless otherwise set forth. An asterisk (*) indicates a control example.

DESCRIPTION OF SPECIFIC EMBODIMENTS

EXAMPLE I*

In this control Example I*, 100 parts of tetralin are place in an opaque reaction vessel to which no light is admitted. Oxygen gas is bubbled in at room temperature (25° C.) and atmospheric pressure for 24 hours. At the end of this period, the reaction mixture is analyzed by GCMS to determine the content of: A - alpha tetralol; B - alpha tetralone; and C - alpha-tetralin-hydroperoxide. Conversion of tetralin was calculated.

In this control Example, Conversion is essentially zero and none of products A, B, or C is identified.

EXAMPLE II*

In this control Example II*, the procedure of Example I* is duplicated—except that the reaction mixture is irradiated with a 450 watt medium pressure mercury—vapor lamp, the output of which included a substantial portion of wave-length below about 2000 Å.

Analysis of the reaction mixture indicates that very little of the desired alcohol or ketone is obtained and substantial quantities of undesirable degradation products are formed.

EXAMPLE III

In this Example, which represents best mode of treating a cyclohexene charge, the charge (100 parts) is placed together with 5 parts of acetophenone in a reaction vessel to which light is admitted. The light which irradiates the charge is derived from a 450 watt medium pressure mercury-vapor lamp which is fitted the "A Sleeve" supra of Pyrex glass which absorbs radiation below about 2800 Å. Thus irradiation is conducted with light of wave length above about 2800 Å.

Irradiation is carried out as oxygen gas is bubbled through the charge at room temperature (25° C.) and atmospheric pressure for 24 hours. At the end of this period, the reaction mixture is analyzed.

Conversion is 19.9%,
Selectivity to cyclohexen-1-hydroperoxide is 50%,
Selectivity to cyclohexen-1-ol is 10.7%
Selectivity to cyclohexen-1-one is 24.1%

EXAMPLE IV

In this Example, which represents the best mode without sensitizer of treating a tetralin charge, the charge (100 parts) is placed in a reaction vessel to which light is admitted. The light which irradiates the charge is derived from a 450 watt medium pressure mercury-vapor lamp which is fitted with the "A Sleeve" of Pyrex glass supra which absorbs radiation below about 2800 Å. Thus the irradiation is conducted with light of wave length above about 2800 Å.

Irradiation is carried out as oxygen gas is bubbled through the charge at room temperature (25° C.) and atmospheric pressure for 24 hours. At the end of this period, the reaction mixture is analyzed.

Conversion is 6.3%
Selectivity to alpha-tetralol is 22.3%
Selectivity to alpha-tetralone is 18.4%
Selectivity to alpha-tetralin-hydroperoxide is 59.3%

EXAMPLES V–XVIII

In each of these Examples, the procedure of Example IV is duplicated except that there are added 5 parts of sensitizer per 100 parts of charge tetralin. In Examples XVII and XVIII, the absorption Sleeve C is employed which cuts off radiation below 4000 Å. In Example IV–XV, the cut-offs are 2800 Å and 3300 Å as indicated.

For each Example, there are set forth:
(i) the photoinitiator/sensitizer;
(ii) Cut-off (Å) below which no irradiation contacts the reaction mixture;
(iii) A—the Conversion i.e the w % of charge converted to products;
(iv) B—the Selectivity to alpha-tetralol i.e. the w % of alpha-tetralol as a percentage of the converted alpha-tetralol with respect to the total converted products;
(v) C—the Selectivity to alpha-tetralone;
(vi) D—the Selectivity to alpha-tetralin hydroperoxide.

TABLE

| Example | Sensitizer | Cut-off | A | B | C | D |
|---|---|---|---|---|---|---|
| V | none | 2800 | 6.3 | 22.3 | 18.4 | 59.3 |
| VI | none | 3300 | 4.1 | 17.9 | 16.4 | 65.7 |
| VII | Benzophenone | 2800 | 12.9 | 44.8 | 19.3 | 14.6 |
| VIII | " | 3300 | 8.9 | 41.8 | 26.1 | 22.1 |
| IX | Acetophenone | 2800 | 11.0 | 37.1 | 25.1 | 37.7 |
| X | " | 3300 | 11.5 | 30.6 | 22.5 | 46.8 |
| XI | 2-butanone | 2800 | 12.6 | 26.6 | 22.1 | 51.3 |
| XII | " | 3300 | 7.5 | 21.0 | 19.5 | 59.5 |
| XIII | Acetone | 2800 | 8.1 | 25.3 | 20.9 | 53.8 |
| XIV | " | 3300 | 6.8 | 20.2 | 19.3 | 60.6 |
| XV | Xanthone | 2800 | 5.9 | 48.1 | 24.2 | — |
| XVI | " | 3300 | 8.7 | 41.2 | 29.4 | 29.4 |
| XVII | " | 4000 | 1.5 | 46.6 | 38.2 | 15.2 |
| XVIII | RuCl$_2$ dipyridyl complex | 4000 | 6.9 | 58.4 | 39.1 | — |

EXAMPLES XIX–XXXVI

In each of these Examples, the procedure of Examples V–XVIII is duplicated except that the charge composition is 100 parts of cyclohexene. The data set forth in the following Table include:
(i) the photoinitiator/sensitizer;
(ii) the Cut-off (Å)
(iii) E—the Conversion
(iv) G—the Selectivity to 2-cyclohexene-hydroperoxide
(v) F—the Selectivity to 2-cyclohexenene-1-ol
(vi) H—the Selectivity to 2-cyclohexene-1-one

TABLE

| Example | Sensitizer | Cut-off Å | E | F | G | H |
|---|---|---|---|---|---|---|
| XIX | Benzophenone | 2800 | 18.7 | 19.2 | 39.3 | 29.8 |
| XX | " | 3300 | 17.3 | 20.1 | 51.7 | 25.6 |
| XXI | " | 4000 | 13.8 | 18.0 | 60.4 | 18.2 |
| XXII | Acetophenone | 2800 | 19.9 | 10.7 | 50.0 | 24.1 |
| XXIII | " | 3300 | 16.7 | 9.3 | 57.0 | 20.2 |
| XXIV | " | 4000 | 8.6 | 12.7 | 68.9 | 15.0 |
| XXV | 2-butanone | 2800 | 20.0 | 7.2 | 56.5 | 20.2 |

TABLE-continued

| Example | Sensitizer | Cut-off Å | E | F | G | H |
|---|---|---|---|---|---|---|
| XXVI | " | 3300 | 7.2 | 3.6 | 74.1 | 13.5 |
| XXVII | " | 4000 | 2.9 | — | 89.8 | 10.2 |
| XXVIII | Acetone | 2800 | 13.8 | 6.2 | 63.1 | 12.0 |
| XXIX | " | 3300 | 7.7 | 1.4 | 71.8 | 14.9 |
| XXX | Xanthone | 2800 | 4.5 | 11.7 | 12.9 | 55.5 |
| XXXI | " | 3300 | 7.5 | 13.2 | 37.9 | 35.6 |
| XXXII | " | 4000 | 6.5 | 11.2 | 63.2 | 21.0 |
| XXXIII | RuCl₂ dipyridyl complex | 4000 | 3.6 | 42.2 | 10.1 | 47.8 |
| XXXIV | none | 2800 | 12.9 | 5.7 | 65.3 | 17.4 |
| XXXVI | " | 3300 | 4.3 | 5.2 | 78.6 | 12.8 |
| XXXVI | " | 4000 | 0.6 | — | 100.0 | — |

Although this invention has been illustrated by reference to specific embodiments, it will be apparent to those skilled in the art that various charges and modifications may be made which clearly fall within the scope of the invention.

What is claimed:

1. The method

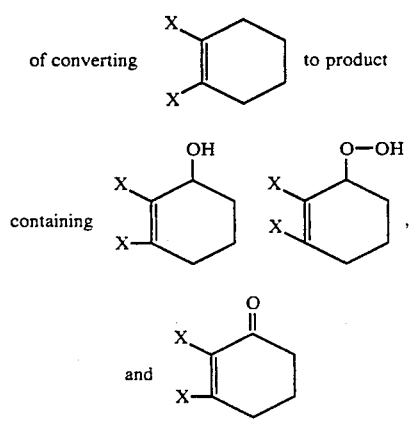

of converting ... to product containing ... and ...

which comprises
maintaining in liquid phase, under photo-oxidation conditions, a charge liquid containing

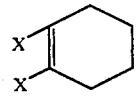

wherein X is hydrogen or together both X's form a 1,3-butadiene chain cyclized to form a benzene ring;

contacting said charge liquid with oxidizing agent during a photooxidation reaction;

irradiating said charge liquid with radiation containing wave lengths of 2000 Å–7000 Å during a photooxidation reaction thereby forming reaction medium containing oxidized charge liquid containing

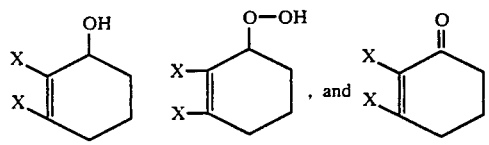

and recovering said reaction medium containing oxidized charge liquid containing

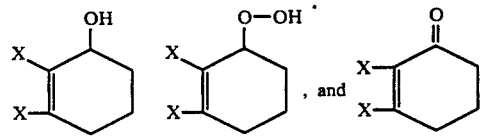

2. The method claimed in claim 1 wherein said charge is tetralin.

3. The method claimed in claim 1 wherein said charge is cyclohexene.

4. The method claimed in claim 1 wherein said photooxidizing conditions include temperature of 0° C.–150° C. at 0–200 psig.

5. The method claimed in claim 1 wherein said oxidizing agent is air, oxygen, or oxygen-enriched air.

6. The method claimed in claim 1 wherein said light contains wave lengths of above 2800 Å.

7. The method claimed in claim 1 wherein said light contains wave lengths of 2800 Å–3000 Å.

8. The method claimed in claim 1 wherein said photooxidation reaction is carried out in the presence of a photoinitiator/sensitizer.

9. The method claimed in claim 1 wherein said photooxidation reaction is carried out in the presence of, as photoinitiator/sensitizer, an aliphatic ketone.

10. The method claimed in claim 1 wherein said photooxidation reaction is carried out in the presence of, as photoinitiator/sensitizer, an aromatic ketone.

11. The method claimed in claim 1 wherein said photooxidation reaction is carried out in the presence of, as photoinitiator/sensitizer, a compound of Fe, Co, Ni, Ru, Rh, Pd, Os, Ir, or Pt.

12. The method of converting tetralin to product containing alpha-tetralol, alpha tetralone, and alpha-tetralone hydroperoxide which comprises
maintaining in liquid phase, under photo-oxidation conditions, a charge liquid containing tetralin;
contacting said charge liquid containing tetralin with oxygen during a photooxidation reaction at 0° C.–150° C. and 0–200 psig;
irradiating said charge liquid containing tetralin with radiation containing wave lengths of 2000 Å–7000 Å thereby forming reaction medium containing alpha-tetralol, alpha tetralone, and alpha-tetralone hydroperoxide; and
recovering said reaction medium containing alpha-tetralol, alpha tetralone, and alpha-tetralone hydroperoxide.

* * * * *